USOO9572597B2

United States Patent
Adinolfi

(10) Patent No.: US 9,572,597 B2
(45) Date of Patent: Feb. 21, 2017

(54) OPTICAL TROCAR TIP PROTECTOR

(71) Applicant: Covidien LP, Mansfield, MA (US)

(72) Inventor: Amanda Adinolfi, Wallingford, CT (US)

(73) Assignee: Covidien LP, Mansfield, MA (US)

( * ) Notice: Subject to any disclaimer, the term of this patent is extended or adjusted under 35 U.S.C. 154(b) by 280 days.

(21) Appl. No.: 14/309,145

(22) Filed: Jun. 19, 2014

(65) Prior Publication Data

US 2015/0088073 A1  Mar. 26, 2015

Related U.S. Application Data

(60) Provisional application No. 61/881,727, filed on Sep. 24, 2013.

(51) Int. Cl.
*A61B 17/34* (2006.01)

(52) U.S. Cl.
CPC .... *A61B 17/3494* (2013.01); *A61B 2017/3454* (2013.01); *A61B 2090/038* (2016.02)

(58) Field of Classification Search
CPC . A61B 17/3494; A61B 17/34; A61B 17/3496; A61B 1/00154; A61B 2017/00362; A61M 5/3202
USPC .............. 206/363, 438; 604/164.08; 606/185
See application file for complete search history.

(56) References Cited

U.S. PATENT DOCUMENTS

| | | | | |
|---|---|---|---|---|
| 2,812,206 A | * | 11/1957 | Brunn | A01K 97/00 294/170 |
| 3,867,946 A | * | 2/1975 | Huddy | A61M 16/0666 128/207.18 |
| 4,331,767 A | * | 5/1982 | Nakajima | C12Q 1/00 422/82 |
| 5,215,450 A | * | 6/1993 | Tamari | A61M 1/0031 138/119 |
| 7,931,622 B2 | | 4/2011 | Beling et al. | |
| 2002/0063074 A1 | * | 5/2002 | Simm | A61M 5/008 206/366 |
| 2005/0067308 A1 | | 3/2005 | Thompson et al. | |
| 2008/0009894 A1 | | 1/2008 | Smith | |
| 2010/0324488 A1 | | 12/2010 | Smith | |

* cited by examiner

*Primary Examiner* — Katherine M Shi

(57) ABSTRACT

A trocar tip protector includes a housing having a first inlet and a second inlet adjacent to each other. The first inlet is configured to receive and frictionally retain a tip of a trocar sleeve. The second inlet is configured to receive and frictionally retain a tip of a trocar obturator. The housing may be formed by extruding a generally tubular structure and then bending the generally tubular structure into a generally U-shaped configuration that positions the trocar sleeve and the trocar obturator substantially parallel relative to each other when the trocar sleeve tip is inserted into the first inlet of the housing and when the trocar obturator tip is inserted into the second inlet of the housing.

9 Claims, 2 Drawing Sheets

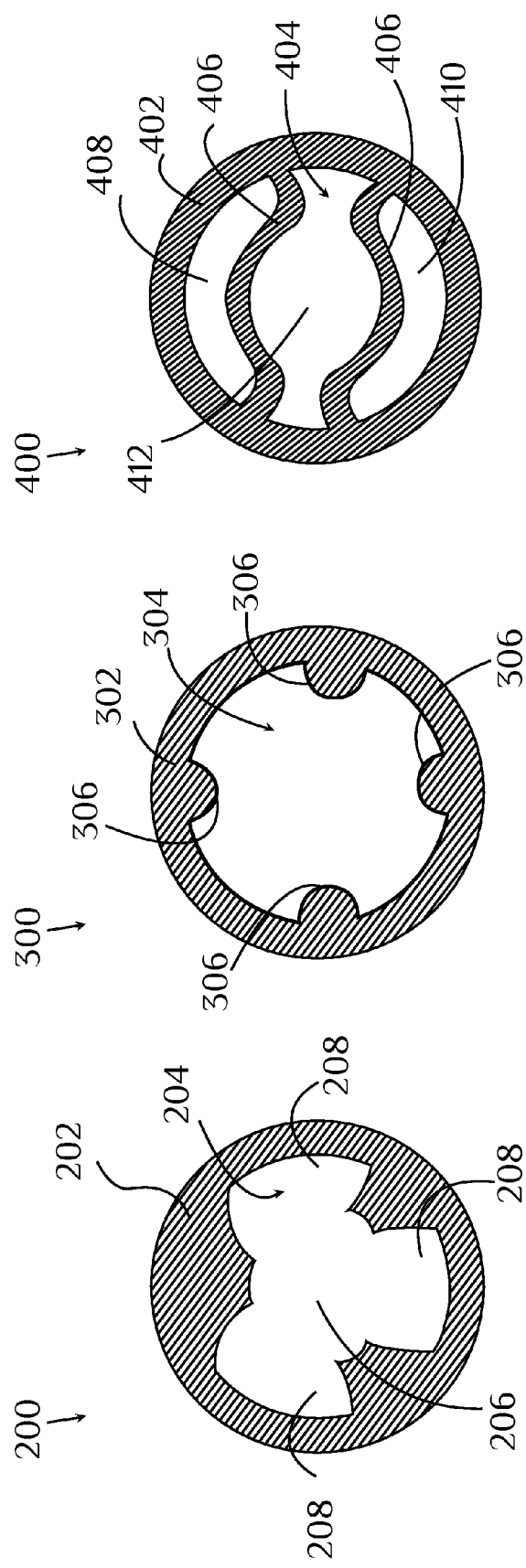

OPTICAL TROCAR TIP PROTECTOR

CROSS-REFERENCE TO RELATED APPLICATION

The present application claims the benefit of and priority to U.S. Provisional Application Ser. No. 61/881,727, filed Sep. 24, 2013, the entire contents of which are incorporated herein by reference.

BACKGROUND

Technical Field

The present disclosure relates to trocar tip protectors for trocar assemblies. More particularly, the present disclosure relates to trocar assembly optical trocar tip protectors providing protection for tips of a trocar sleeve and obturator.

Background of Related Art

A trocar assembly is a surgical instrument that is used to gain access to a body cavity. A trocar assembly generally comprises two major components: a trocar sleeve composed of a trocar housing and a trocar cannula; and a trocar obturator. The trocar sleeve, having the trocar obturator inserted therethrough, is directed through the skin to access a body cavity. Once the body cavity is accessed, laparoscopic or arthroscopic surgery and endoscopic procedures may be performed. In order to penetrate the skin, the distal end of the trocar sleeve is placed against the skin that has been previously cut with a scalpel. The trocar obturator is then used to penetrate the skin and access the body cavity. By applying pressure against the proximal end of the trocar obturator, the sharp point of the trocar obturator is forced through the skin until it enters the body cavity. The trocar sleeve is inserted through the perforation made by the obturator and the obturator is withdrawn, leaving the trocar sleeve as an access way to the body cavity.

The proximal end portion of the trocar sleeve is typically adjoined by a housing that defines a chamber having an open distal end portion that communicates with the interior lumen defined by the trocar sleeve. An obturator, or other elongated surgical instruments, axially extend into and are withdrawn from the trocar sleeve through the proximal end portion of the chamber. Trocar obturators are typically designed with a sharp tip that is used to puncture an abdominal wall. Trocar packaging designs should ensure that the sharp tip of the trocar obturator does not puncture packaging material that forms a sterile barrier. If the material used for the sterile barrier is not strong enough to prevent puncture on its own, an ancillary form of protection may be required.

Typically, a tip protector is used for trocar assemblies, especially trocar obturators. Current tip protectors generally consist of a cap that completely encapsulates the sharp tip of the trocar obturator. Such caps completely obscure the view of the tip of the trocar obturator as it sits in the unopened package. It is, however, important for those using these instruments to be able to visibly identify the tip style prior to use. This is especially important when a variety of different obturator tip styles are available.

In addition to the tip problem discussed above, problems exist when providing packaging for surgical trocar assemblies. Some trocar assembly designs require that the trocar assembly be packaged with the obturator not inserted into the trocar sleeve, as over time this would cause a seal within the trocar cannula to become deformed. If this is the case, a two-piece device assembly must be packaged.

It is generally preferred to dispense a single assembly from the trocar assembly package rather than a two-piece assembly. Reasons for preferring a one-piece assembly include reducing the opportunity for components to roll off from the sterile barrier as well as the desire to keep the obturator and trocar sleeve matched up together when dispensing or unpacking numerous different trocar types.

As a result, it is readily apparent that a trocar assembly optical trocar tip protector is needed which overcomes the shortcomings of prior trocar assembly optical trocar tip protectors. The present disclosure provides such a trocar assembly optical trocar tip protector.

SUMMARY

The following presents a simplified summary of the claimed subject matter in order to provide a basic understanding of some aspects of the claimed subject matter. This summary is not an extensive overview of the claimed subject matter. It is intended to neither identify key or critical elements of the claimed subject matter nor delineate the scope of the claimed subject matter. Its sole purpose is to present some concepts of the claimed subject matter in a simplified form as a prelude to the more detailed description that is presented later.

The present disclosure, in accordance with various embodiments thereof, may relate to a trocar assembly that includes a trocar sleeve having a trocar sleeve tip; a trocar obturator having a trocar obturator tip; a trocar tip protector that is extruded and bent into a shape that positions a trocar sleeve and a trocar obturator parallel relative to each other when the trocar sleeve tip is inserted into a first inlet of the trocar tip protector and when the trocar obturator tip is inserted into a second inlet of the trocar tip protector.

In embodiments, the trocar tip protector may be generally U-shaped. The trocar tip protector may be transparent or semi-transparent. The trocar tip protector may have an interior cross-section that is non-circular. The interior cross-section of the trocar tip protector may be configured to accommodate components of different diameters.

In accordance with other embodiments of the present disclosure, there is provided a trocar tip protector that includes a housing having a first inlet and a second inlet adjacent to each other; the first inlet configured to receive and frictionally retain a tip of a trocar sleeve; the second inlet configured to receive and frictionally retain a tip of a trocar obturator, wherein the housing is formed by extruding a generally tubular structure and then bending the generally tubular structure into a generally U-shaped configuration that positions the trocar sleeve and the trocar obturator substantially parallel relative to each other when the trocar sleeve tip is inserted into the first inlet of the housing and when the trocar obturator tip is inserted into the second inlet of the housing.

Further scope of applicability of the present disclosure will become apparent from the detailed description given hereinafter. However, it should be understood that the detailed description and specific examples, while indicating embodiments of the present disclosure, are given by way of illustration only, since various changes and modifications within the spirit and scope of the present disclosure will become apparent to those skilled in the art from this detailed description.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiment(s) given below, serve to explain the principles of the disclosure, wherein:

FIG. 2 is a front, cross-sectional view of an optical trocar tip protector, in accordance with an alternative embodiment of the present disclosure;

FIG. 3 is a front, cross-sectional view of an optical trocar tip protector, in accordance with a further embodiment of the present disclosure; and FIG. 4 is a front, cross-sectional view of an optical trocar tip protector, in accordance with another embodiment of the present disclosure.

Figure 1:
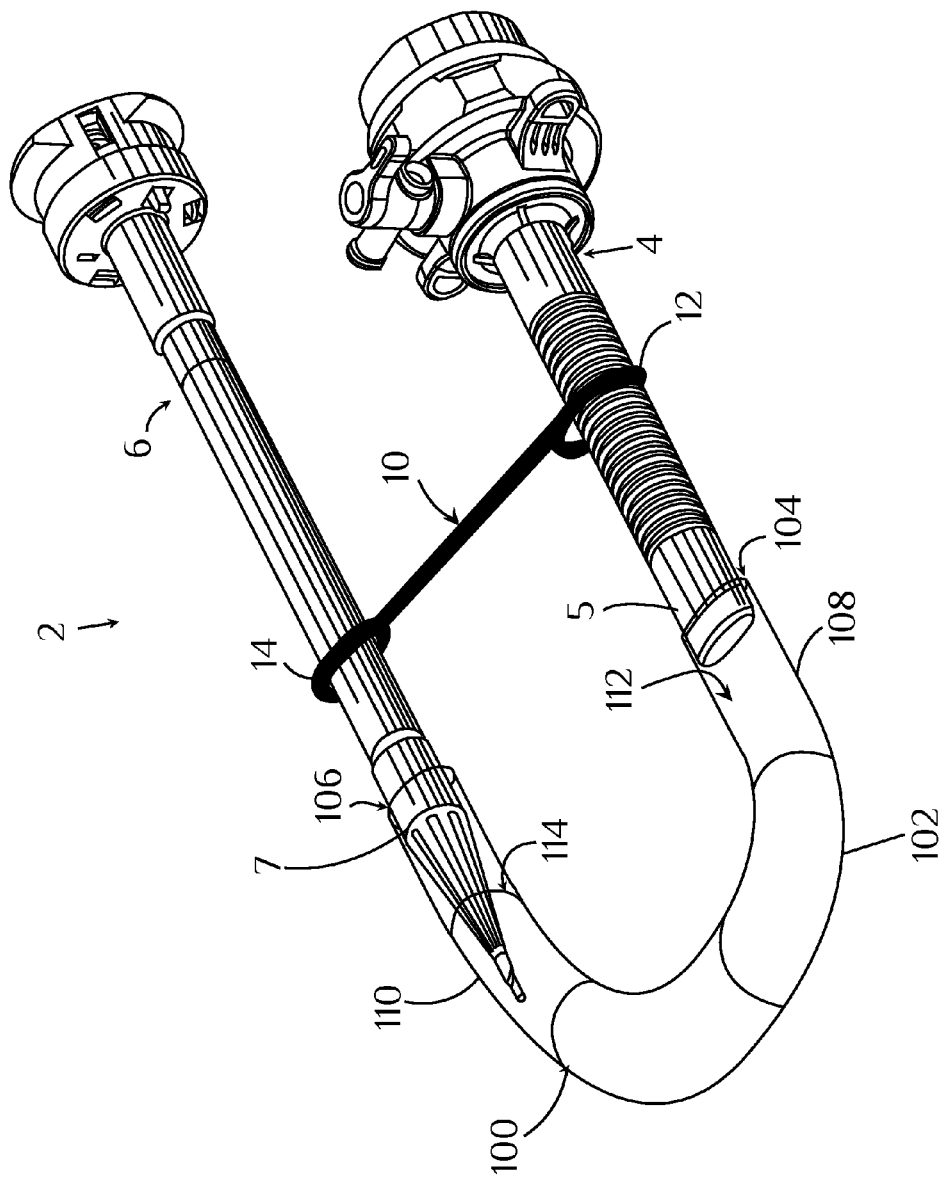
FIG. 1 is a perspective view of a trocar assembly including an optical trocar tip protector, in accordance with an embodiment of the present disclosure.

The figures depict embodiments of the present disclosure for purposes of illustration only. One skilled in the art will readily recognize from the following discussion that alternative embodiments of the structures and methods illustrated herein may be employed without departing from the principles of the present disclosure described herein.

DETAILED DESCRIPTION

Embodiments of the present disclosure are described hereinbelow with reference to the accompanying drawings. However, it is to be understood that the disclosed embodiments are merely exemplary of the disclosure and may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure.

For the purposes of promoting an understanding of the principles of the present disclosure, reference will now be made to the exemplary embodiments illustrated in the drawings, and specific language will be used to describe the same. It will nevertheless be understood that no limitation of the scope of the present disclosure is thereby intended. Any alterations and further modifications of the inventive features illustrated herein, and any additional applications of the principles of the present disclosure as illustrated herein, which would occur to one skilled in the relevant art and having possession of this disclosure, are to be considered within the scope of the present disclosure.

With reference to FIGS. 1 to 4, an optical trocar tip protector for trocar assembly components, for example, a trocar sleeve 4 and a trocar obturator 6 of a trocar assembly 2, is disclosed and designated as 100. The optical trocar tip protector 100 includes an extruded plastic, unitary housing member 102 that serves as a tip protector for trocar assembly components 4, 6. The optical trocar tip protector 100 further supports the trocar obturator 6 adjacent the trocar sleeve 4.

In accordance with an embodiment of the present disclosure, the entire housing member 102 of the optical trocar tip protector 100 is extruded from a compliant, transparent or semi-transparent material, for example, an elastomer. In another embodiment, the optical trocar tip protector 100 is extruded in a straight configuration initially and is then bent into the shape shown in FIG. 1. In this manner, the cost and complexity of molding the optical trocar tip protector 100 is avoided and can be manufactured at a lower cost. While the present optical trocar tip protector 100 is disclosed as being constructed from a particular material, those skilled in the art will appreciate the optical trocar tip protector 100 may be manufactured from a variety of similar materials without departing from the spirit of the present disclosure.

Unitary housing member 102 which, when bent into the configuration shown in FIG. 1, has two open ends 104, 106 that are adjacent to each other and that lead into substantially parallel first and second sleeves 108, 110, respectively. The first and second sleeves 108, 110 maintain the trocar sleeve 4 and trocar obturator 6 in a predefined relationship when both are mounted within the optical trocar tip protector 100.

As those skilled in the art will certainly appreciate, trocar sleeves are slightly larger in diameter than the trocar obturators that pass therethrough. Thus, in order to accommodate slightly different sized components being inserted therein (even though the extrusion process has provided each sleeve 108, 110 with an inner diameter that is roughly equal to one another), the structure of the interior of the optical trocar tip protector 100 can have a variety of different cross-sectional shapes, such as those shown in FIGS. 2-4, as described in further detail herein below. Each one of these cross-sectional shapes allows the sleeves 108, 110 of the optical trocar tip protector 100 to expand to match the size of the component being inserted therein, with sufficient frictional retention thereof to retain a respective trocar sleeve 4 and trocar obturator 6 within sleeves 108, 110 during transport and prior to use.

The first sleeve 104 includes an inlet 112 adjacent an end thereof. The inlet 112 is formed with an internal structure shaped and dimensioned to frictionally engage the trocar sleeve 4, for example, as it is positioned within the optical trocar tip protector 100. Because the optical trocar tip protector 100 is formed of compliant material, the first sleeve 108 will accommodate a variety of instrument diameters.

As with the first sleeve 108, the second sleeve 110 includes an inlet 114 adjacent an end thereof. The inlet 114 is shaped and dimensioned to frictionally engage the trocar obturator 6, for example, as it is positioned within the optical trocar tip protector 100. Because the optical trocar tip protector 100 is formed of compliant material, the second sleeve 110 will accommodate a variety of instrument diameters while still functioning in accordance with the underlying concepts of the present disclosure. Because the optical trocar tip protector 100 is formed of a transparent or semi-transparent material, viewing of the trocar sleeve 4 and the trocar obturator 6 by a user is possible prior to opening the sterile package (not shown). Therefore, tips 5, 7 of the trocar sleeve 4 and trocar obturator 6 can be easily identified.

The present construction also provides protection for the tips 5, 7 of both the trocar sleeve 4 and the trocar obturator 6 as the optical trocar tip protector 100 stops the respective tips 5, 7 of the trocar sleeve 4 and trocar obturator 6 from moving relative to each other or from contacting the sterile barrier. This may help eliminate the possibility that the tips 5, 7 of the trocar sleeve 4 and the trocar obturator 6 inadvertently puncture the sterile barrier prior to use.

Trocar assembly 2 can include a mechanical link 10 further stabilizing the orientation and position of trocar sleeve 4 relative to trocar obturator 6. Link 10 includes a first hook member 12 detachably connected to trocar sleeve 4 and a second hook member 14 detachably connected to trocar obturator 6.

In one embodiment, as shown in FIG. 2, a trocar tip protector 200, similar to trocar tip protector 100, has an interior cross-section configuration 202 configured to accommodate trocar sleeves and obturators of various diameters. The interior cross-section configuration 202 has an overall non-circular shape. Specifically, an inner periphery or inlet 204 of trocar tip protector 200 has a generally circular inner cavity 206 and a plurality of winged recesses 208 formed thereabout.

In one embodiment, as shown in FIG. 3, a trocar tip protector 300, similar to trocar tip protector 100, has an interior cross-section configuration 302 configured to accommodate trocar sleeves and obturators of various diameters. The interior cross-section configuration 302 has an overall non-circular shape. Specifically, an inner periphery or inlet 304 of trocar tip protector 300 has a plurality of arcuate ribs 306 extending therein forming a rounded, cross-like cross-sectional shape.

In one embodiment, as shown in FIG. 4, a trocar tip protector 400, similar to trocar tip protector 100, has an interior cross-section configuration 402 configured to accommodate trocar sleeves and obturators of various diameters. The interior cross-section configuration 402 has an overall non-circular shape. Specifically, an inner periphery or inlet 404 of trocar tip protector 400 has a pair of undulating, deformable members 406 extending therein forming a first arcuate cavity 408, a second arcuate cavity 410, and a third cavity 412 disposed therebetween configured for disposal of at least one of a trocar sleeve and a trocar obturator.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of presently disclosed embodiments. Thus the scope of the embodiments should be determined by the appended claims and their legal equivalents, rather than by the examples given.

Persons skilled in the art will understand that the devices and methods specifically described herein and illustrated in the accompanying drawings are non-limiting exemplary embodiments. The features illustrated or described in connection with one exemplary embodiment may be combined with the features of other embodiments. Such modifications and variations are intended to be included within the scope of the present disclosure. As well, one skilled in the art will appreciate further features and advantages of the present disclosure based on the above-described embodiments. Accordingly, the present disclosure is not to be limited by what has been particularly shown and described, except as indicated by the appended claims.

What is claimed is:

1. A trocar assembly, comprising:
    a trocar sleeve having a trocar sleeve tip;
    a trocar obturator having a trocar obturator tip;
    a trocar tip protector, comprising:
        a housing having a first inlet and a second inlet adjacent to each other;
        the first inlet configured to receive and frictionally retain the tip of the trocar sleeve;
        the second inlet configured to receive and frictionally retain the tip of the trocar obturator, at least one of the first inlet or the second inlet including a pair of deformable, undulating members defining an arcuate first cavity, an arcuate second cavity, and an arcuate third cavity disposed between the first and second cavities, the pair of undulating members being configured to flex outwardly upon the third cavity receiving one of the tip of the trocar sleeve or the tip of the trocar obturator, wherein the housing is formed by extruding a generally tubular structure and then bending the generally tubular structure into a generally U-shaped configuration that positions the trocar sleeve and the trocar obturator substantially parallel relative to each other when the trocar sleeve tip is inserted into the first inlet of the housing and when the trocar obturator tip is inserted into the second inlet of the housing.

2. The trocar assembly according to claim 1, wherein the trocar tip protector is transparent.

3. The trocar assembly according to claim 1, wherein the trocar tip protector is semitransparent.

4. The trocar assembly according to claim 1, wherein the trocar tip protector has an interior cross-section that is non-circular.

5. The trocar assembly according to claim 4, wherein the interior cross-section of the trocar tip protector is configured to accommodate components of different diameters.

6. A trocar tip protector, comprising:
    a housing having a first inlet and a second inlet adjacent to each other;
    the first inlet configured to receive and frictionally retain a tip of a trocar sleeve;
    the second inlet configured to receive and frictionally retain a tip of a trocar obturator, at least one of the first inlet or the second inlet including a pair of deformable, undulating members defining an arcuate first cavity, an arcuate second cavity, and an arcuate third cavity disposed between the first and second cavities, the pair of undulating members being configured to flex outwardly upon the third cavity receiving one of the tip of the trocar sleeve or the tip of the trocar obturator, wherein the housing is formed by extruding a generally tubular structure and then bending the generally tubular structure into a generally U-shaped configuration that positions the trocar sleeve and the trocar obturator substantially parallel relative to each other when the trocar sleeve tip is inserted into the first inlet of the housing and when the trocar obturator tip is inserted into the second inlet of the housing.

7. The trocar tip protector according to claim 6, wherein the housing is transparent.

8. The trocar tip protector according to claim 6, wherein the housing is semitransparent.

9. The trocar tip protector according to claim 6, wherein at least one of the first inlet or the second inlet is configured to accommodate components of different diameters.

* * * * *